United States Patent [19]
Pastor et al.

[11] Patent Number: 5,817,850
[45] Date of Patent: Oct. 6, 1998

[54] FERROCENE BIS(PHOSPHONITE) LIGANDS AND COMPLEXES FOR TRANSITION-METAL-CATALYZED REACTIONS

[75] Inventors: Stephen D. Pastor, Danbury, Conn.; Sai P. Shum, Hightstown, N.J.

[73] Assignee: Ciba Specialty Chemicals Corporation, Tarrytown, N.Y.

[21] Appl. No.: 961,130

[22] Filed: Oct. 30, 1997

[51] Int. Cl.⁶ .............................. C07F 17/02; B01J 31/00
[52] U.S. Cl. .................. 556/14; 556/19; 556/28; 556/144; 502/155; 502/162; 568/878; 568/429; 568/444; 568/451; 564/407; 558/335; 585/277
[58] Field of Search .................. 556/14, 19, 28, 556/144; 568/429, 444, 451, 878; 502/155, 162; 564/407; 558/335; 585/277

[56] References Cited

PUBLICATIONS

I.É. Nifant'er et al., Russian J. Gen. Chem. (English Translation), 65, 682 (1995).
Ferrocenes by Antonio Togni and Tamio Hayashi, VCH Publishers, Weinheim–New York, 1995.
G. Pioda and A. Togni, in Chimia 51, Nr. 8/9, 613 (1997).

*Primary Examiner*—Porfirio Nazario-Gonzalez
*Attorney, Agent, or Firm*—Luther A. R. Hall

[57] ABSTRACT

The synthesis of new sterically hindered ferrocene bis(phosphonites) of formula I

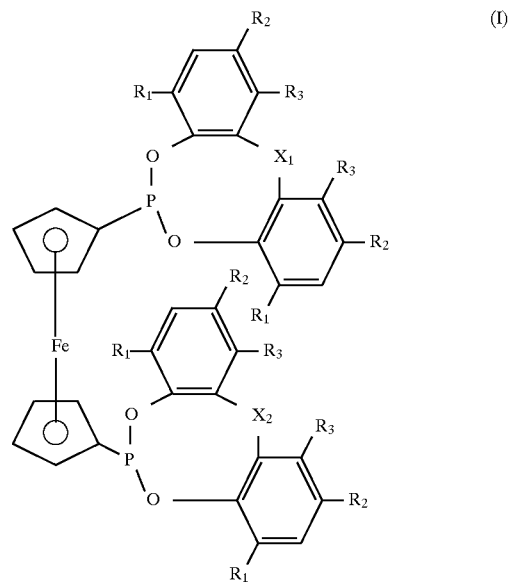

the synthesis of the corresponding transition-metal complexes and the use of these complexes in transition-metal-catalyzed reactions are described.

20 Claims, No Drawings

FERROCENE BIS(PHOSPHONITE) LIGANDS AND COMPLEXES FOR TRANSITION-METAL-CATALYZED REACTIONS

The instant invention pertains to the synthesis of new sterically hindered ferrocene bis(phosphonite) ligands, the corresponding transition-metal complexes thereof, and the use of such complexes for transition-metal-catalyzed reactions.

BACKGROUND OF THE INVENTION

Transition-metal-catalyzed reactions have become an important organic chemical synthetic procedure. The instant ligands and complexes provide an important contribution to this field of organic syntheses.

A comprehensive review of the chemistry of the ferrocenes has recently appeared as "Ferrocenes", edited by Antonio Togni and Tamio Hayashi, VCH Publishers, Weinheim, N.Y., 1995.

The synthesis of ferrocenyl bis(phosphonite) ligands containing five- and six-membered rings has been reported by I. É. Nifant'ev et al., Russian J. Gen. Chem. (English translation), 65, 682 (1995). The rhodium complexes of these ligands are reported to hydrosilate acetophenone in low yields (35–68%). The ligands of the Russian reference are structurally quite different from the instant ligands.

G. Pioda and A. Togni, in Chimia 51, Nr 8/9, 613 (1997) report an alternative approach to chiral ferrocenyl ligands containing P—N and P—O bonds. These ferrocenyl ligands are disubstituted on one ring of the ferrocene moiety and clearly differ from the instant ferrocenes.

OBJECTS OF THE INVENTION

The objects of the invention are the synthesis of new sterically hindered ferrocene bis(phosphonites), the synthesis of the corresponding transition-metal complexes, and the use of these ligands and complexes in transition-metal-catalyzed reactions.

DETAILED DISCLOSURE

The instant invention pertains to the synthesis of new sterically hindered ferrocene bis(phosphonites) of formula I

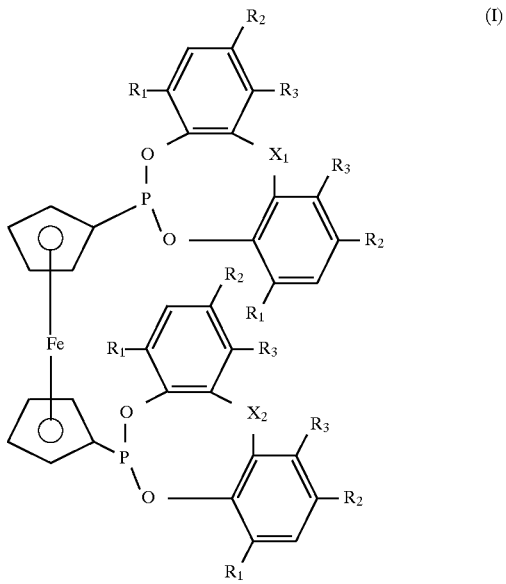

wherein
$R_1$, $R_2$ and $R_3$ are independently hydrogen, alkyl of 1 to 20 carbon atoms, aralkyl of 7 to 15 carbon atoms or aryl of 6 to 10 carbon atoms, $X_1$ and $X_2$ are independently a direct bond, alkylidene of 1 to 20 carbon atoms, sulfur or selenium.

Preferably, $R_1$ is tert-butyl.

Preferably, $R_2$ is hydrogen, methyl, methoxy or tert-butyl; most preferably, tert-butyl.

Preferably $R_3$ is hydrogen or methyl; most preferably, hydrogen.

Preferably, $X_1$ and $X_2$ are each a direct bond, methylene or ethylidene.

The instant invention also pertains to the transition-metal complex of the ferrocene bis(phosphonite) of formula I where the transition-metal is selected from the group consisting of the metals of group VIII.

Preferably the transition metal is rhodium, palladium or platinum; most preferably rhodium.

The advantages of the instant ligands are that they are hydrolytically stable; that they are stable to reaction conditions encountered in the transition-metal-catalyzed reactions; and they give higher product yields compared to reactions of the prior art.

The transition-metal-catalyzed reactions of the instant invention are hydrosilations; hydrogenations; hydrocyanations; cross-couplings; carbonylations; and hydrocarbonylations.

Of especial interest is a process for the hydrogenation of an ethylenically unsaturated compound; for the hydrosilation of a ketone; or for the cross-coupling of an amine and an aromatic halogen compound using a transition-metal and a ferrocenyl bisphosphonite of formula I.

The following examples are for illustrative purposes only and are not to be construed to limit the scope of the instant invention in any manner whatsoever.

EXAMPLE 1

1,1'-Bis[2,4,8,10-tetrakis(tert-butyl)-dibenzo[d,f][1,3,2]dioxaphosphepin-6-yl]ferrocene To a solution of 9.5 g (50 mmol) of ferrocene in 250 mL of hexane is added dropwise 67 mL of a 1.6M solution of n-butyl lithium at ambient temperature. The reaction mixture is stirred for 20 minutes and then to the resultant red suspension is added 12.0 g (103 mmol) of N,N,N',N'-tetramethylethylenediamine. A slight exotherm of 10° C. is observed. The reaction mixture is then heated at reflux for two hours during which time an orange suspension forms. The reaction mixture is cooled to room temperature and 100 mL of tetrahydrofuran is then added. The reaction mixture is cooled to −40° C. Then to the cooled reaction mixture is added dropwise a solution of 51.8 g (109 mmol) of 2,4,8,10-tetrakis(tert-butyl)-6-chloro-dibenzo[d,f][1,3,2] dioxaphosphepin in 100 mL of tetrahydrofuran. The reaction mixture is allowed to warm to ambient temperature after the addition is complete. The reaction mixture is then heated at reflux for six hours. After cooling, the mixture is filtered and the filtrate is concentrated under reduced pressure. The residue formed is triturate with 150 mL of hexane. The resultant solid is recrystallized from acetonitrile/tetrahydrofuran mixture to give 25 g (47% yield) of a light brown solid.

Mass spectrometry: m/z=1064

$^{31}P\{^1H\}$ nmr $(C_6D_6)$=193 ppm

EXAMPLE 2

1,1'-Bis[2,4,8,10-tetrakis(tert-butyl)-12H-dibenzo[d,g][1,3,2]dioxaphosphocin-6-yl]ferrocene The general procedure of Example 1 is followed using 3.5 g (18.8 mmol) of ferrocene in 30 mL of hexane, 25 mL of a 1.6M hexane solution of n-butyl lithium, 4.5 g (38.7 mmol) of N,N,N',N'-tetramethylethylenediamine and 20 g (41 mmol) of 2,4,8,10-tetrakis(tert-butyl)-6-chloro-12H-dibenzo[d,g][1,3,2]dioxaphosphocin in 100 mL of tetrahydrofuran. The residue is triturated with hexane and the resultant solid is recrystallized from an acetonitrile/tetrahydrofuran mixture to give 12 g (58.5% yield) of a light brown solid.

Mass spectrometry: m/z=1092

$^{31}P\{^1H\}$ nmr $(C_6D_6)$=177 ppm

EXAMPLE 3

1,1'-Bis[2,4,8,10-tetrakis(tert-butyl)-12-methyl-dibenzo[d,g][1,3,2]dioxaphosphocin-6-yl]ferrocene Following the general procedure of Example 2, and substituting an equivalent amount of 2,4,8,10-tetrakis(tert-butyl)-6-chloro-12-methyl-dibenzo[d,g][1,3,2] dioxaphosphocin for 2,4,8,10-tetrakis(tert-butyl)-6-chloro-12H-dibenzo[d,g][1,3,2]dioxaphosphocin the title compound is prepared.

EXAMPLE 4

Dimeric Rhodium Complex of 1,1'-Bis[2,4,8,10-tetrakis(tert-butyl)-dibenzo[d,f][1,3,2]dioxaphosphepin-6-yl]ferrocene To a mixture of 426 mg (0.4 mmol) of the ferrocenyl bisphosphonite prepared in Example 1 and 98 mg (0.2 mmol) of chloro(1,5-cyclooctadiene)rhodium(I) dimer is added 2 mL of benzene-$d_6$. The reaction mixture is stirred for five minutes at ambient temperature to give a solution of the rhodium complex (title compound).

$^{31}P\{^1H\}$ nmr $(C_6D_6)$=169.2 ppm; (doublet, $^1J$ (Rh,P)=272.6 Hz)

EXAMPLE 5

Monomeric Rhodium Complex of 1,1'-Bis[2,4,8,10-tetrakis(tert-butyl)-dibenzo[d,f][1,3,2]dioxaphosphepin-6-yl]ferrocene To the solution of the dimeric rhodium complex obtained in Example 4 is added dropwise 25 mg (0.3 mmol) of pyridine. The reaction mixture is stirred at ambient temperature for five minutes to give a solution of the monomeric rhodium complex of the title compound.

$^{31}P\{^1H\}$ nmr $(C_6D_6)$=178.9 ppm; (doublet of doublets, $^2J(P_1,P_2)$=54.8 Hz; $^1J$ (Rh,P$_1$)=242.9 Hz); 169.0 ppm (doublet of doublets, $^2J(P_1,P_2)$=54.8 Hz; $^1J$ (Rh,P$_1$)=267.2 Hz)

EXAMPLE 6

Cationic Rhodium Complex of 1,1'-Bis[2,4,8,10-tetrakis(tert-butyl)-dibenzo[d,f][1,3,2]dioxaphosphepin-6-yl]ferrocene The procedure of Example 4 is repeated using 32.9 mg (0.031 mmol) of 1,1'-bis[2,4,8,10-tetrakis(tert-butyl)-dibenzo[d,f][1,3,2]dioxaphosphepin-6-yl]ferrocene prepared in Example 1 and 12.6 mg (0.031 mmol) of bis(bicyclo[2.2.1]hepta-2,5-diene)-rhodium(I) perchlorate in 2 mL of methanol and 0.5 mL of tetrahydrofuran.

$^{31}P\{^1H\}$ nmr $(C_6D_6)$=165.2 ppm; (doublet, $^1J$ (Rh,P)=211.90 Hz)

EXAMPLE 7

Dimeric Rhodium Complex of 1,1'-Bis[2,4,8,10-tetrakis(tert-butyl)-12H-dibenzo[d,g][1,3,2]dioxaphosphocin-6-yl]ferrocene Following the general procedure of Example 4, the title compound is prepared from the ferrocenyl bisphosphonite of Example 2.

EXAMPLE 8

Monomeric Rhodium Complex of 1,1'-Bis[2,4,8,10-tetrakis(tert-butyl)-12H-dibenzo[d,g][1,3,2]dioxaphosphocin-6-yl]ferrocene Following the general procedure of Example 5, the title compound prepared from the dimeric rhodium complex prepared in Example 7.

EXAMPLE 9

Cationic Rhodium Complex of 1,1'-Bis[2,4,8,10-tetrakis(tert-butyl)-12H-dibenzo[d,g][1,3,2]dioxaphosphocin-6-yl]ferrocene Following the general procedure of Example 6, the title compound is prepared from the ferrocenyl bisphosphonite of Example 3.

EXAMPLE 10

Dimeric Rhodium Complex of 1,1'-Bis[2,4,8,10-tetrakis(tert-butyl)-12-methyl-dibenzo[d,g][1,3,2]dioxaphosphocin-6-yl]ferrocene Following the general procedure of Example 4, the title compound is prepared from the ferrocenyl bisphosphonite of Example 3.

EXAMPLE 11

Monomeric Rhodium Complex of 1,1'-Bis[2,4,8,10-tetrakis(tert-butyl)-12-methyl-dibenzo[d,g][1,3,2]dioxaphosphocin-6-yl]ferrocene Following the general procedure of Example 5, the title compound prepared from the dimeric rhodium complex prepared in Example 10.

EXAMPLE 12

Cationic Rhodium Complex of 1,1'-Bis[2,4,8,10-tetrakis(tert-butyl)-12-methyl-dibenzo[d,g][1,3,2]dioxaphosphocin-6-yl]ferrocene Following the general procedure of Example 6, the title compound is prepared from the ferrocenyl bisphosphonite of Example 3.

EXAMPLE 13

Hydrosilation of Acetophenone

To a mixture of 426 mg (0.4 mmol) of 1,1'-bis[2,4,8,10-tetrakis(tert-butyl)-dibenzo[d,f][1,3,2]dioxaphosphepin-6-yl]ferrocene prepared in Example 1 and 98 mg (0.2 mmol) of chloro(1,5-cyclooctadiene)rhodium(I) dimer is added 2 mL of toluene. The reaction mixture is stirred for 30 minutes and then the resultant solution of the rhodium complex is added to a solution of 1.17 mL (10 mmol) of acetophenone and 1.86 mL (10 mmol) of diphenylsilane in 5 mL of toluene. The resultant cloudy suspension is stirred at ambient temperature for 16 hours. The reaction mixture is then added to a mixture of 1.5N sodium hydroxide/methanol solution. The reaction mixture is extracted three times with diethyl ether and the combined organic phase is dried over anhydrous sodium sulfate. The organic phase is isolated by filtration and the volatiles are removed under reduced pressure to give 1.15 g of a yellow residue from which $^1$H nmr analysis shows a 78% conversion of the starting acetophenone to sec-phenethyl alcohol.

EXAMPLE 14

Hydrosilation of Acetophenone

The procedure of Example 13 is repeated using 426 mg (0.4 mmol) of the ferrocenyl bis(phosphonite) prepared in Example 1, 98 mg (0.2 mmol) of chloro(1,5-cyclooctadiene)rhodium(I) dimer, 1.17 mL (10 mmol) of acetophenone, 1.86 mL (10 mmol) of diphenylsilane and a total of 7 mL of tetrahydrofuran. The conversion of the starting acetophenone to sec-phenethyl alcohol after 15 minutes is 94.5%. $^1$H nmr analysis of the reaction mixture after 16 hours indicated a 97.2% conversion to sec-phenethyl alcohol. Workup of the reaction mixture gave 1.1 g (90% yield) of sec-phenethyl alcohol.

EXAMPLE 15

Hydrogenation of Dimethyl Itaconate

A mixture of 33 mg (0.031 mmol) of the ferrocenyl bis(phosphonite) prepared in Example 1 and 12 mg (0.031 mmol) of bis(bicyclo[2.2.1]hepta-2,5-diene)rhodium(I) perchlorate in 2 mL of methanol/tetrahydrofuran (1:1) solution is stirred for two hours. Then, to the resultant solution of rhodium complex is added a solution of 490 mg (3.1 mmol) of dimethyl itaconate and 13 mL of methanol in a pressure reactor. The reactor is then pressurized to 1018 psi with hydrogen and the reaction is stirred at ambient temperature for 88 hours. $^1$H nmr analysis of the reaction mixtures shows a 100% conversion of dimethyl itaconate starting material to product. Workup of the reaction mixture gives 492 mg (99% yield) of desired dimethyl 2-methylsuccinate.

EXAMPLE 16

Cross-coupling Reaction of an Amine with a Halobenzene

To a mixture of 10 g (54 mmol) of 3-phenoxyaniline, 7.85 g (50 mmol) of bromo-benzene, 110 mg (0.125 mmol) of tris(dibenzylideneacetone)-dipalladium(0), 400 mg of the ferrocenyl bis(phosphonite) prepared in Example 1 and 7.8 g of sodium tert-butoxide is added 100 mL of dioxane. The reaction mixture is heated at 110 c. for 16 hours. The desired product N-phenyl-3-phenoxyaniline is detected by mass spectroscopy (m/z=261).

EXAMPLE 17

Pt(II) Complex of 1,1'-Bis[2,4,8,10-tetrakis(tert-butyl)-dibenzo[d,f][1,3,2]dioxaphosphepin-6-yl]ferrocene The title complex is prepared by following the procedure of Example 4 using the ferrocenyl ligand of Example 1 and (1,5-cyclooctadiene)platinum(II) dichloride.

What is claimed is:

1. A new sterically hindered ferrocene bis(phosphonite) of formula I

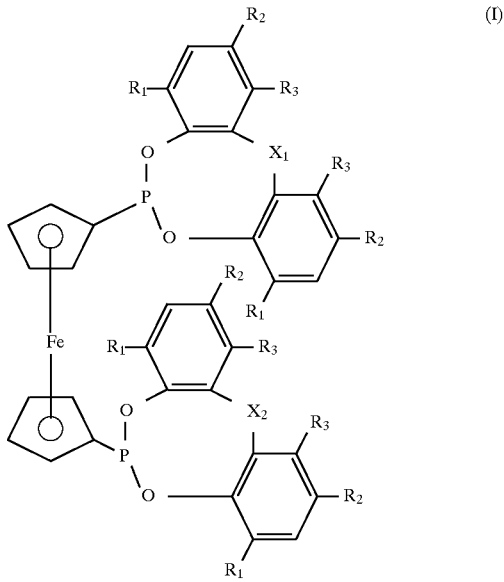

wherein $R_1$, $R_2$ and $R_3$ are independently hydrogen, alkyl of 1 to 20 carbon atoms, aralkyl of 7 to 15 carbon atoms or aryl of 6 to 10 carbon atoms, $X_1$ and $X_2$ are independently a direct bond, alkylidene of 1 to 20 carbon atoms, sulfur or selenium.

2. A compound of formula I according to claim 1 wherein $R_1$ is tert-butyl.

3. A compound of formula I according to claim 1 wherein $R_2$ is hydrogen, methyl, methoxy or tert-butyl.

4. A compound according to claim 3 wherein $R_2$ is tert-butyl.

5. A compound of formula I according to claim 1 wherein $R_3$ is hydrogen or methyl.

6. A compound according to claim 5 wherein $R_3$ is hydrogen.

7. A compound of formula I according to claim 1 wherein $X_1$ and $X_2$ are each a direct bond, methylene or ethylidene.

8. A transition-metal complex of the ferrocene bis(phosphonite) of formula I

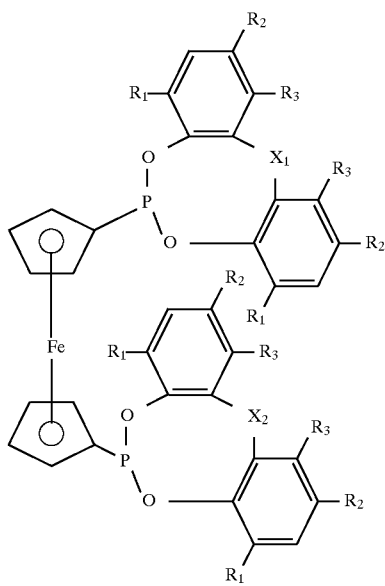

(I)

wherein $R_1$, $R_2$ and $R_3$ are independently hydrogen, alkyl of 1 to 20 carbon atoms, aralkyl of 7 to 15 carbon atoms or aryl of 6 to 10 carbon atoms, $X_1$ and $X_2$ are independently a direct bond, alkylidene of 1 to 20 carbon atoms, sulfur or selenium, and the transition-metal is selected from the group consisting of the transition metals of group VIII.

9. A complex according to claim 8 where in the compound of formula I, $R_1$ and $R_2$ are each tert-butyl, $R_3$ is hydrogen; $X_1$ and $X_2$ are each a direct bond, methylene or ethylidene; and the transition metal is rhodium, palladium or platinum.

10. A complex according to claim 8 wherein the transition-metal is rhodium.

11. A complex according to claim 8 wherein the transition-metal is platinum.

12. A complex according to claim 8 wherein the transition-metal is palladium.

13. A transition-metal-catalyzed hydrosilation reaction of an aldehyde or ketone to form an alcohol which is catalyzed by a complex according to claim 8.

14. A transition-metal-catalyzed hydrogenation reaction of an ethylenically unsaturated compound to form the corresponding saturated compound which is catalyzed by a complex according to claim 8.

15. A transition-metal-catalyzed cross-coupling reaction of an aryl halide with an amine to give a substituted arylamine which is catalyzed by a complex according to claim 8.

16. A transition-metal-catalyzed hydrocarbonylation reaction of an alkene with carbon monoxide and hydrogen to form an aldehyde which is catalyzed by a complex according to claim 8.

17. A transition-metal-catalyzed hydrocyanation reaction of an alkene with hydrogen cyanide to form the corresponding nitrile which is catalyzed by a complex according to claim 8.

18. A process for the hydrogenation of an ethylenically unsaturated compound using a catalyst comprising a complex of a transition-metal and a ferrocenyl bisphosphonite of formula I according to claim 1.

19. A process for the hydrosilation of a ketone to an alcohol using a catalyst comprising a complex of a transition-metal and a ferrocenyl bisphosphonite of formula I according to claim 1.

20. A process for the cross-coupling of an amine with an aromatic halogen compound using a catalyst comprising a complex of a transition-metal and a ferrocenyl bisphosphonite of formula I according to claim 1.

* * * * *